United States Patent
Hanin

(10) Patent No.: US 6,688,311 B2
(45) Date of Patent: Feb. 10, 2004

(54) METHOD FOR DETERMINING EFFECT OF A CLOSTRIDIAL TOXIN UPON A MUSCLE

(75) Inventor: Lisa D. Hanin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 47 days.

(21) Appl. No.: 10/099,602

(22) Filed: Mar. 14, 2002

(65) Prior Publication Data

US 2003/0178029 A1 Sep. 25, 2003

(51) Int. Cl.[7] .............................................. A61B 19/00
(52) U.S. Cl. ....................................... 128/898; 600/300
(58) Field of Search ........................................... 128/898

(56) References Cited

U.S. PATENT DOCUMENTS

| | | | | |
|---|---|---|---|---|
| 3,689,668 A | * | 9/1972 | Emile Leon Piette et al. ................. | 514/555 |
| 4,758,730 A | * | 7/1988 | Bazin et al. ........... | 250/559.22 |
| 4,997,657 A | * | 3/1991 | Horrobin et al. ........... | 424/401 |
| 5,437,291 A | | 8/1995 | Pasricha et al. | |
| 5,670,484 A | | 9/1997 | Binder | |
| 5,714,468 A | | 2/1998 | Binder | |
| 5,766,606 A | | 6/1998 | Brady | |
| 5,989,545 A | | 11/1999 | Foster et al. | |
| 6,063,768 A | | 5/2000 | First | |
| 6,113,915 A | | 9/2000 | Aoki et al. | |
| 6,139,845 A | | 10/2000 | Donovan | |
| 6,143,306 A | | 11/2000 | Donovan | |
| 6,261,572 B1 | | 7/2001 | Donovan | |
| 6,265,379 B1 | | 7/2001 | Donovan | |

FOREIGN PATENT DOCUMENTS

| | | |
|---|---|---|
| WO | WO 96/33273 | 10/1996 |
| WO | WO 98/07864 | 2/1998 |
| WO | WO 99/03483 | 1/1999 |
| WO | WO 99/17806 | 4/1999 |
| WO | WO 00/10598 | 3/2000 |
| WO | WO 00/15245 | 3/2000 |
| WO | WO 00/24419 | 5/2000 |
| WO | WO 00/57897 | 10/2000 |
| WO | WO 00/62746 | 10/2000 |
| WO | WO 00/74703 A2 | 12/2000 |
| WO | WO 01/21213 A2 | 3/2001 |

OTHER PUBLICATIONS

Bitzer et al (Journal abstract from the Archives of Otolaryngology—Head & Neck Surgery Apr. 1997 ; 123(4): 389–92.).*
Pribitkin et al (Journal abstract from the Archives of Otolaryngology—Head & Neck Surgery Apr. 1997; 123(4): 321–26.).*
Guerrissi et al (Journal abstract from the Annals of Plastic Surgery 1997 39/5 (447–453)).*
Guerrissi et al (Journal article from the Annals of Plastic Surgery 1997 39/5 (447–453)).*
J. O Guerrissi, injection of botulinum toxin A into orbicularis oculi muscle for the treatment of crow's feet., and the discussion thereof, Plastic and reconstructive surgery (United States) May 2000, 105 (6) (2219–2228).*
Aoki, R., et al., Preclinical update on BOTOX® (botulinum toxin type A)–purified neurotoxin complex relative to other botulinum neurotoxin preparations, *European Journal of Neurology*, 1999 6 (suppl 4): S3–S10.
Brach, Jennifer S. et al., Measuring Fatigue Related to Facial Muscle Function, *Arch Phys Med Rehabil*, vol. 76, Oct. 1995, pp 95–98.

(List continued on next page.)

*Primary Examiner*—Corrine McDermott
*Assistant Examiner*—Thomas Sweet
(74) *Attorney, Agent, or Firm*—Stephen Donovan

(57) ABSTRACT

A skin topographical method for quantifying pharmacodynamic parameters of a paralytic effect of a Clostridial toxin, such as a botulinum toxin upon a muscle, such as a frontalis muscle.

8 Claims, 2 Drawing Sheets

OTHER PUBLICATIONS

Carruthers, J. et al, Treatment of Glabellar Frown Lines with C. Botulinum–A Exotoxin, *J. Dermatol Surg Oncol*, Jan. 1992: 18(1):17–21.

Corcuff, P. et al., Skin relief and aging, *J. Soc. Cosmet. Chem*, 34, (Jul. 1983), pp 177–190.

Doggweiler, R., Botulinum toxin type a causes diffuse and highly selective atrophy of rat prostate, *Neurourol Urodyn*, 1998; 17(4): 363.

Dressler, D. et al., Electromyographic Quantification of the Paralysing Effect of Botulinum Toxin in the Sternocleidomastoid Muscle, *European Neurology*, 2000; 43, pp 13–16.

Fauci, Anthony et al., *Harrison's Principles of Internal Medicine*, 14$^{th}$ Edition, 1998 by McGraw Hill.

Fridlund, Alan, et al., Guidelines for Human Electromyographic Research, *The Society for Psychophysiological Research, Inc.*, Vol 23, No 5, 1986, pp 567–589.

Grove, Gary L. et al., Objective Methods for Assessing Skin Surface Topography Noninvasively, *Cutaneous Investigation in Health and Disease*, 1989 by Marcel Dekker, Inc., Chapter One, pp 1–32.

Grove, Gary L. et al., Skin replica analysis of photodamaged skin after therapy with tretinoin emollient cream, *Journal of the American Academy of Dermatology*, Vol 25, No 2, Part 1, Aug. 1991, pp 231–237.

Guerrissi, Jorge, et al., Local Injection into Mimetic Muscles of Botulinum Toxin A for the Treatment of Facial Lines, *Annals of Plastic Surgery*, Vol 39, No 5, Nov. 1997, pp 447–453.

Heckmann, Marc, et al., Quantification of the efficacy of botulinum toxin type A by digital image analysis, *J Am Acad Dermatol*, 2001, 45, PP 508–514, Published online May 23, 2001, pp 1–7.

Johnson, Eric A., Biomedical Aspects of Botulinum Toxin, *J. Ttoxicol Toxin Reviews*, 18(1) 1999, pp 1–15, Abstract.

Leyden, James J., et al., Treatment of photodamaged facial skin with topical tretinoin, *Journal of the American Academy of Dermatology*, Vol 21, No 3, Part 2, Sep. 1989, pp 638–644.

Pennock, Jennifer D., et al., Relationship between Muscle Activity of the Frontalis and the Associated Brow Displacement, *Plast Reconstr Surg*, Nov., 1999 104 (6) pp 1789–1787.

Senior, M.A., Botox and the management of pectoral spasm after subpectoral implant inseration, *Plast. Reconstr. Surg* Jul. 2000; 106,(1) pp. 224–225.

Tassinary, Louis G., et al., A Psychometric Study of Surface Electrode Placements for Facial Electromyographic Recording: I. The Brow and Cheek Muscle Regions, *Psychophysiology*, 1989, Vol 26, No 1, pp 1–16, Abstract.

Van Boxtel, A., et al., Amplitude and Bandwidth of the Frontalis Surface EMG: Effects of Electrode parameters, *Psychophysiology*, 1984, Vol 21, No 6, pp 699–707, Abstract.

Vitti, Mathias, et al., Electromyographic Investigation of Procerus and Frontalis Muscles, *Electromyogr. Clin. Neurophysiol.*, 1976, 16, pp 227–236.

\* cited by examiner

METHOD FOR DETERMINING EFFECT OF A CLOSTRIDIAL TOXIN UPON A MUSCLE

BACKGROUND

The present invention relates to methods for determining an effect of a Clostridial toxin upon a muscle. In particular, the present invention relates to use of a dermal topography method for determining an effect of a Clostridial toxin upon a facial muscle.

Movement of the face can be due to contractions of muscles underlying the skin and different muscles can move different parts of the face. For example, elevation of the brow results from contraction of the frontalis muscle. Electromyographic methods have been used to study the activity of various facial muscles. See e.g. Fridlund A. et al., *Guidelines for Human Electromyographic Research, Psychophysiology* 1986; 23(5): 567–590; Vitti M, et al., *Electromyographic Investigation of Procerus and Frontalis Muscles*, Electromyogr. clin. Neurophysiol. 1976,16: 227–236, and; Tassinary L. et al., *A Psychometric Study of Surface Electrode Placements for Facial Electromyographic Recording: I. The Brow and Cheek Muscle Regions*, Psychophysiology 1989; 26(1): 1–16.

In particular, electromyography, including surface electromyography (sEMG) has been used to investigate activity of the frontalis muscle and resultant brow displacement. See e.g. van Boxtel A, et al., *Amplitude and bandwidth of the frontalis surface EMG: Effects of electrode parameters*, Psychophysiology 1984; 21(6): 699–707, and; Pennock J. D., et al., *Relationship between muscle activity of the frontalis and the associated brow displacement*, Plast Reconstr Surg November 1999; 104(6): 1789–1797.

Additionally, it is known to study skin topography by making a silicone rubber negative replica (a mold) of a skin surface area. The mold captures three dimensional details of the skin surface and computerized image analysis of skin line density, depths and length analysis shown can be carried out thereon. Grove, G. L., et al, *Objective method for assessing skin surface topography noninvasively*, chapter one, pages 1–32 of *Cutaneous Investigation in Health and Disease*, edited by Leveque J-L., Marcel Dekker, Inc. (1989). This method has been used to study how microfurrows on the forearm can increase in depth from about 33 $\mu$m in children to up to about 100 $\mu$m in the elderly. Corcuff P. et al., *Skin relief and aging*, J Soc Cosmet Chem 1983; 34:177–190. The same silicone rubber impression method has been used to examine the effect of a topical cream to treat photodamaged skin, as by reduction of periorbital (crows feet) wrinkles. Leyden J. J., et al., *Treatment of photodamaged facial skin with topical tretinoin*, J Am Acad Dermatol 1989; 21(3) (part 2): 638–644, and; Grove G. L., et al., *Skin replica analysis of photodamaged skin after therapy with tretinoin emollient cream*, J Am Acad Dermatol 1991; 25(2) (part 1): 231–237.

Botulinum Toxin

The anaerobic, gram positive bacterium Clostridium botulinum produces a potent polypeptide neurotoxin, botulinum toxin, which causes a neuroparalytic illness in humans and animals known as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botutinum toxin type A is the most lethal natural biological agent known to man. bout 50 picograms of botulinum toxin (purified neurotoxin complex) type A[1] is a $LD_{50}$ in mice. One unit (U) of botulinum toxin is defined as the $LD_{50}$ upon intraperitoneal injection into female Swiss Webster mice weighing 18–20 grams each. Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. The botulinum toxins apparently binds with high affinity to cholinergic motor neurons, is translocated into the neuron and blocks the release of acetylcholine.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus, hemifacial spasm and cervical dystonia.

[1]Avaible from Allegran, Inc. of Irvine, Calif. under the tradeneme BOTOX®.

Botulinum toxin type B has also been approved by the FDA for the treatment of cervical dystonia. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture.

It has been reported that botulinum toxin type A has been used in clinical settings as follows:

(1) about 75–250 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

It is also known that injection of a botulinum toxin into facial muscles can, by weakening the injected muscles, result in a decrease of hyperkinetic wrinkles in the skin overlying the paralyzed muscles. See e.g. Carruthers A. et al., *The treatment of glabellar furrows with botulinum A exotoxin*, J Dermatol Surg Oncol 1990 January; 16(1):83.

It is known to use a botulinum toxin to treat: intrathecal pain (see e.g. U.S. Pat. No. 6,113,915); paragangliomas (see e.g. U.S. Pat. No. 6,139,845); otic disorders (see e.g. U.S. Pat. No. 6,265,379); pancreatic disorders (see e.g. U.S. Pat. Nos. 6,143,306 and 6,261,572); migraine (see e.g. U.S. Pat. No. 5,714,468); smooth muscle disorders (see e.g. U.S. Pat. No. 5,437,291); prostate disorders, including prostatic hyperplasia (see e.g. WO 99/03483 and Doggweiler R., et al *Botulinum toxin type A causes diffuse and highly selective atrophy of rat prostate*, Neurourol Urodyn 1998; 17(4):363); autonomic nerve disorders, including hyperplasic sweat glands (see e.g. U.S. Pat. No. 5,766,606); wound healing (see e.g. WO 00/24419); reduced hair loss (see e.g. WO 00/62746); skin lesions (see e.g. U.S. Pat. No. 5,670,484), and; neurogenic inflammatory disorders (see e.g. U.S. Pat. No. 6,063,768).

Additionally it has been disclosed that targeted botulinum toxins (i.e. with a non-native binding moiety) can be used to treat various conditions (see e.g. U.S. Pat. No. 5,989,545, as well as WO 96/33273; WO 99/17806; WO 98/07864; WO 00/57897; WO 01/21213; WO 00/10598.

A botulinum toxin has been injected into the pectoral muscle to control pectoral spasm. See e.g. Senior M., *Botox and the management of pectoral spasm after subpectoral implant insertion*, Plastic and Recon Surg, July 2000, 224–225.

Both liquid stable formulations and pure botulinum toxin formulations have been disclosed (see e.g. WO 00/15245 and WO 74703) as well as topical application of a botulinum toxin (see e.g. DE 198 52 981).

Typically, a Clostridial toxin, such as a botulinum toxin, is administered locally and directly into a target tissue, such as a skeletal muscle, by intramuscular or subcutaneous injection. Entry of a Clostridial toxin into the circulatory system is undesirable, since botulism or tetanus can result. Additionally, entry of a Clostridial toxin into the systemic circulation typically results in generation of antibodies against the toxin. The presence of antibodies leads to a loss or diminishment of a desired clinical response, such as a muscle paralysis. Thus, methodologies for determination of bioavailability of a Clostridial toxin practiced in regard to an intravenously or orally administered pharmaceutical are neither relevant nor applicability with regard to a locally (i.e. intravenous or subcutaneous) administered Clostridal toxin.

Unfortunately, therefore methodologies which examine a physiological fluid (i.e. blood, urine) are of little or no value to determine bioavailability of a Clostridial toxin to a target muscle or muscle group, due to the local (non-systemic) administration and effect of the toxin. Thus, currently available analytical techniques to perform classical absorption, distribution, biotransformation and elimination studies on an oral or intravenously administered drugs cannot be used.

Botulinum toxin has been injected into facial muscles, such as the orbicularis oculis, corrugator supercilii and frontalis muscles for the cosmetic purpose of reducing certain facial wrinkles, and it is known to use electromyographic and/or photographic techniques to assess the efficacy of such injections. Guerrissi J. et al., *Local injection into mimetic muscles of botulinum toxin A for the treatment of facial lines*, Ann Plast Surg 1997; 39(5):447–53. Electromyography has also been used to assess the effect of injection of a botulinum toxin into the sternocleidomastoid muscle for treatment of cervical dystonia. Dressler D. et al., *Electromyographic quantification of the paralysing effect of botulinum toxin in the stemocleidomastoid muscle*, Eur Neurol 2000; 43:13–16. In sEMG the surface electrodes are placed at fixed distances from the injection point, typically 1 cm and 3 cm from the injection point. The surface electrodes can be used to measure the amplitude and area of a compound muscle action potential (CMAP) during maximal voluntary contraction of the injected muscle. One expects to find that CMAP decreases with the onset of muscle paralytic effect and to increase as the paralytic effect wears off.

Unfortunately, electromyographic methods for determining an effect of a Clostridial toxin, such as a botulinum toxin, upon a muscle or muscle group can be unsatisfactory because of the variability of electrical activity from a particular muscle between patients an even with the same patient in different positions or on different days due to the known vagaries of electrophysiology. For example, repeat surface electromyographic recordings can show significant (i.e. from about 7% to about 20%) variability when taken from the same patient at the same time. Additionally, the extent of maximal voluntary contraction, at which the sEMG recording is taken, can be variable between and among patients.

Photographic methods, such as digital image analysis, have been used to determine efficacy of a botulinum toxin to treat hyperkinetic facial lines. Heckmann M., et al., *Quantification of the efficacy of botulinum toxin type A by digital image analysis*, J Am Acad Dermatol 2001; 45: 508–514. As with electromyographic methods, photographic methods also show significant intra and inter subject variability. Thus, photographic methods for determining an effect of a Clostridial toxin, such as botulinum toxin, upon a muscle or a muscle group can lack precision and accuracy and the quality and value of the images obtained are as variant as the lighting conditions, type of film used, film speed and the film development process used.

Thus both electromyographic and photographic methods for assessing an effect of a botulinum toxin upon a muscle have significant drawbacks and deficiencies and neither of these methods can readily provide a three dimensional permanent record amenable to analysis.

What is needed therefore is a non-invasive method for determining a pharmacodynamic effect (such as a muscle paralytic effect) of a Clostridial toxin, such as a botulinum toxin, upon a muscle or muscle group, which method provides an accurate and precise three dimensional record amendable to computerized analysis.

SUMMARY

My invention fulfills this need and provides a non-invasive method for determining a pharmacodynamic effect (such as a muscle paralytic effect) of a Clostridial toxin, such as a botulinum toxin, upon a muscle or muscle group. Additionally, my method provides an accurate and precise three dimensional record amendable to computerized analysis. The method disclosed herein can comprise the steps of administering a Clostridial toxin to a muscle; making an impression of a feature of a skin surface in proximity to the muscle to which the Clostridial toxin was administered; examining the impression, and; determining onset of paralysis, peak paralysis and duration of paralysis of the muscle by the Clostridial toxin.

The administering step can be carried out by intramuscular injection or subcutaneous injection of the Clostridial toxin. Alternately, a suitable controlled release implant, containing a Clostridial toxin, can be inserted under the skin or within the muscle. Preferably, the muscle is a facial muscle (such as a frontalis muscle) because facial skin can show a more determinable response to injection of a Clostridial toxin into the muscle which underlies the skin. In other words, the skin of the face such as on the forehead has a topography which encompasses easily discernable wrinkles, furrow and lines which can produce a quantifiable response to an intramuscular toxin injection. Thus, a causal connection exists between the paralytic effect of a Clostridial toxin upon a muscle and change in facial topography. I have discovered how to quantify this causality so as to determine pharmocodynamic effects of a Clostridial toxin upon muscles.

Preferably, the Clostridial toxin is a botulinum toxin (such as a botulinum toxin type A, B, C, D, E, F or G) because several botulinum toxins are commercially available and have been used clinically to paralyze various muscles. An embodiment of the present invention encompasses use of from about: 1 unit to about 1,000 units of a botulinum toxin type A (i.e. between about 1–300 units of the BOTOX type A botulinum toxin or between about 1–1000 units of the DYSPORT type botulinum toxin); 10 to 10,000 units of a type B botulinum toxin (such as the MYOBLOC type B botulinum toxin), and; amounts of the other botulinum toxins based on their known differing potencies.

The impression step can comprise applying a polymeric material to the skin surface to thereby obtain a mold which has, on the surface of the mold in contact with the skin surface, a negative replica of a skin surface topography. The examining step can comprise illuminating the negative replica surface of the mold with incident light.

Additionally, the determining step can further comprise determining an extent of diffusion of the Clostridial toxin in the muscle to which the Clostridial toxin was dministered and into a surrounding area. And the determining step can comprise, subsequent to the illuminating step, the step of generating an optical image of the illuminated negative replica surface. Furthermore, the determining step can comprise, subsequent to the generating step, the step of computing a parameter of a skin line present on the negative replica surface.

A detailed embodiment of the present invention is a method for determining a paralytic effect of a botulinum toxin (such as a botulinum toxin type A) upon a facial muscle by: (a) administering a botulinum toxin to a facial muscle by intramuscular injection; (b) making an impression of a feature of a skin surface in proximity to the muscle to which the Clostridial toxin was administered; (c) examining the impression, and; (d) determining onset of paralysis, peak paralysis and duration of paralysis of the muscle by the Clostridial toxin. This method can further comprising the steps of making an electromyographic recording of electrical activity of the facial muscle and photographing the skin surface.

A further detailed embodiment of the present invention is a method for determining a pharmacodynamic effect of a botulinum toxin upon a facial muscle, the method comprising the steps of: (a) administering a botulinum toxin to a facial muscle by intramuscular injection; (b) making an electromyographic recording of electrical activity of the facial muscle; (c) photographing a skin surface in proximity to the muscle to which the Clostridial toxin was administered; (d) making an impression of a feature of the skin surface; (e) examining the impression, and; (f) determining onset of paralysis, peak paralysis and duration of paralysis of the facial muscle by the Clostridial toxin.

The route of administration and amount of Clostridial toxin administered can vary widely according to the particular muscle being injected and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14$^{th}$ edition, published by McGraw Hill). Treatment is carried out so as to substantially avoiding entry of the toxin into the systemic circulation (i.e. by use of subcutaneous or intramuscular injection as opposed to intravenous administration).

The specific dosage appropriate for administration is readily determined by one of ordinary skill in the art according to the factors discussed above. The dosage can also depend upon the size of the muscle to be treated or denervated, and the commercial preparation of the toxin. Generally, it is known that the amount of a Clostridial toxin (such as a botulinum toxin) to be injected is proportional to the mass and level of activity of the muscle tissue to be treated.

The present invention includes within its scope the use of any Clostridial toxin which has a long duration therapeutic effect. For example, neurotoxins made by any of the species of the toxin producing Clostridium bacteria, such as Clostridium botulinum, Clostridium butyricum, and Clostridium beratti can be used or adapted for use in the methods of the present invention. Additionally, all of the botulinum serotypes A, B, C, D, E, F and G can be advantageously used in the practice of the present invention, although type A is the most preferred serotype, as explained above.

"Local administration" means direct injection of the Clostridial into the muscle, subcutaneous or intradermal injection. Systemic routes of administration, such as oral and intravenous routes of administration, are excluded from the scope of the present invention.

The Clostridial toxin (such as a botulinum toxin) used in the present invention botulinum toxin can be a modified Clostridial toxin, that is the toxin can have at least one of its amino acids deleted, modified or replaced, as compared to a native Clostridial toxin. Thus, the Clostridial toxin used can be a recombinant produced Clostidial (i.e. botulinum) toxin or a derivative or fragment thereof.

FIG. 3 is a diagrammatic illustration of a placement of surface EMG electrodes on a patient.

DESCRIPTION

Figure 1:
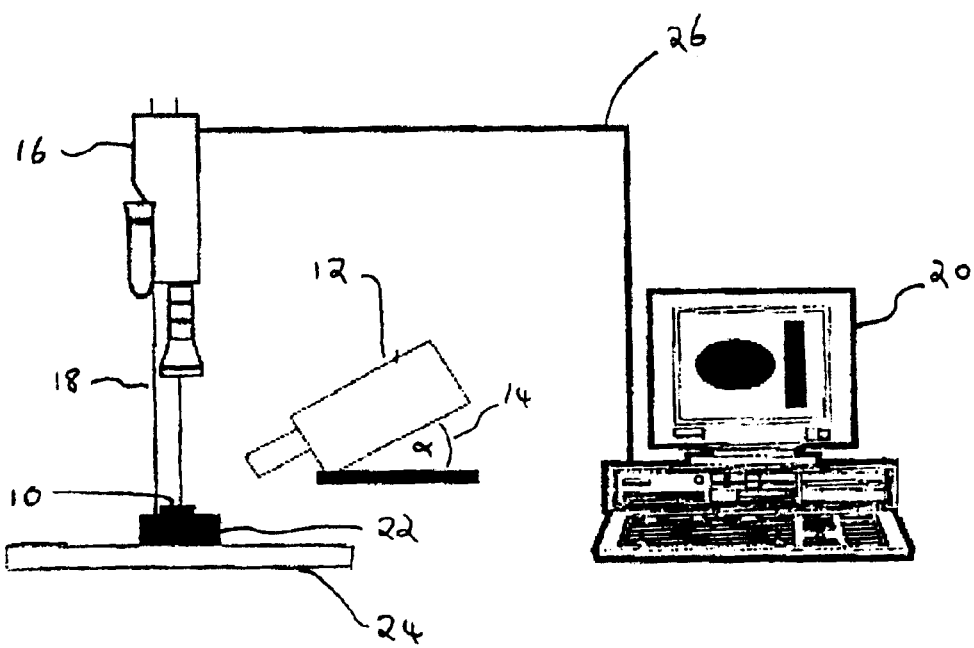
FIG. 1 is a diagrammatic illustration of a digital imaging system for use in a method of the present invention.

My invention is based upon the discovery that a skin surface topographical method can be used to determine an effect of a Clostridial toxin upon a muscle. The effect determined through use of the disclosed method can be a paralytic effect (i.e. inability to contract), including onset of effect, peak effect and duration of paralytic effect of a Clostridial toxin upon a muscle. My skin surface topographical method can proceed by making silicone rubber negative replicas of a skin surface area before and after administration of a Clostridial toxin to a muscle or muscle group of a patient. Imaging profile analysis of the skin surface replica is then carried out.

Previously, skin surface topography methods have been used to assess development of microfurrows in the skin with age, and the efficacy of topically applied creams to treat photodamaged skin. Surprisingly, it has now been discovered that skin topography can be used to assess an effect of a botulinum toxin upon a muscle.

The present invention uses skin topography to determine the parameters of a muscle weakening effect of an intramuscular injection of a Clostridial toxin, such as a botulinum toxin, into a muscle, such as the frontalis muscle. Thus, by practice of my invention skin topography is used to determine, subsequent to injection of a clostridial toxin, that the injected toxin produces a dose-dependent inhibition of maximum voluntary contraction of a muscle, such as the frontalis muscle. The present method thereby provides a way of using facial topography to determine an effect of administration of a Clostridial toxin.

In one embodiment, my invention makes use of the known antiwrinkling effect of a Clostridial toxin, such as a botulinum toxin, as determined from a quantitative facial topography analysis, to quantify various pharmacodynamic and/or neurophysiological properties (profile) of the toxin following intramuscular or subcutaneous injection, into a muscle, such as the frontalis muscle of the forehead. The properties my invention permits quantification of include onset of muscle paralytic effect, peak paralytic effect and duration of the paralytic effect. The purpose of my invention is not to determine if or to what extent a Clostridial toxin has an antiwrinkling effect upon intramuscular injection of the toxin.

In another embodiment, my invention is a method for quantitative assessment of the effect of a Clostridial toxin on muscle activity through use of: (1) a skin surface topography profile; (2) a photographic eyebrow position assessment, and/or; (3) an examination of underlying muscle activity (sEMG).

In the practice of my invention a skin surface topography method is used to make skin surface replicas for the purpose of evaluating a muscle weakening effect of a Clostridial toxin, such as a botulinum toxin, on a muscle, such as the frontalis muscle, following i.e. maximum voluntary contraction of the muscle.

Additionally, a muscle weakening effect of an administered Clostridial toxin upon a muscle, can be determined according to my invention, where the muscle is the frontalis muscle, by quantifying eyebrow displacement. I have discovered that a geometric facial measurement of eyebrow mobility provides for an objective description and evaluation of the effect of a Clostridial toxin on the frontalis muscle. This is achieved by measurements of brow position taken from standardized serial photographs. The digital images are analyzed by software measuring the distance between the inner canthus of the eye and the lower edge of the eyebrow. Graded, sustained frontalis muscle activity correlates with graded, sustained elevation of the eyebrow.

Furthermore, my invention encompasses use of a relationship between frontalis muscle activity, as measured with sEMG, and the associated eyebrow displacement. Measurements by maximum static response assay can be analyzed. Thus subjects are asked to elevate their eyebrows and to view the electromyographic signal to maintain voluntary contractions for 5 seconds at maximum level. My invention with regard to this methodology is to use the known sEMG method to analyze brow displacement as another measure of frontalis muscle activity for the purpose of determining an effect of a Clostridial toxin. Electrophysiological measurements can be used to more directly assess muscle activity and the pharmacodynamic properties of a Clostridial toxin, such as a botulinum toxin. Analysis of surface electromyographical (sEMG) activity of the frontalis muscle can be carried out.

Thus, my invention encompasses use of topographical, electrophysiological and/or photographical image methods as a means of measuring the muscle weakening effect of a Clostridial toxin (such as a botulinum toxin) to a muscle (such as the frontalis muscle), thereby providing a better understanding of the pharmacodynamic properties of Clostridial toxins.

Botulinum toxins for use according to the present invention can be pure botulinum toxins (i.e. the 150 kD type A toxin), can be stored in lyophilized or vacuum dried form in containers under vacuum pressure or be in a liquid format. Prior to lyophilization the botulinum toxin can be combined with pharmaceutically acceptable excipients, stabilizers and/or carriers, such as albumin. The lyophilized or vacuum dried material can be reconstituted with saline or water.

In each of the following examples, the specific amount of a botulinum toxin administered depends upon a variety of factors to be weighed and considered within the discretion of the attending physician and in each of the examples insignificant amounts of botulinum toxin enter appear systemically with no significant side effects.

EXAMPLES

The following examples set forth specific embodiments of the present invention and are not intended to be limiting examples of the scope of my invention.

Example 1

Facial Topography Method for Determining Effect of a Botulinum Toxin Upon Frontalis Muscle A female patient 36 years of age presents with bilateral, symmetrical and moderately severe forehead lines during maximum voluntary contraction of the frontalis muscle.

All make-up and cosmetics are removed from the patient's forehead, which is then cleansed with an alcohol solution. A silicon replica is made of the patients right frontalis during maximum voluntary contraction of the frontalis muscle as follows. The frontalis muscle is identified by having the patient look up and elevate her eyebrows. sEMG is used to confirm frontalis contraction. An adhesive ring 2.4 cm in diameter is positioned over an injection site on the right frontalis. A thin layer of freshly prepared silicon replica mixture (rubber silicon, 2 g, and amyl acetate catalyst, 2 drops) is applied within the adhesive ring on the right side of the forehead during maximum voluntary contraction of the frontalis muscle. The patient is instructed to maintain maximal frontalis muscle contraction for four minutes in which time the silicone polymer sets. After about 5 minutes, the hardened silicon replica is removed. The skin surface replica obtained provides a baseline negative impression (a mold) and record of the skin surface to which the silicone polymer set.

A syringe contained 20 U of a botulinum toxin type A (such as BOTOX) is directed across the frontalis muscle fibers perpendicular to the forehead skin surface and keeping the needle-tip bevel side up, and with the frontalis at rest,10 U of the botulinum toxin is injected bilaterally injections into each of the right and left frontalis muscle, at a position 2.5 cm above the superior arch of the left and right eyebrows, in line with the vertical axis of the center of the pupils. The patient is followed over a 62 week period subsequent to the injection of the botulinum toxin and at each visit additional right frontalis silicon replicas are made.

Figure 2:
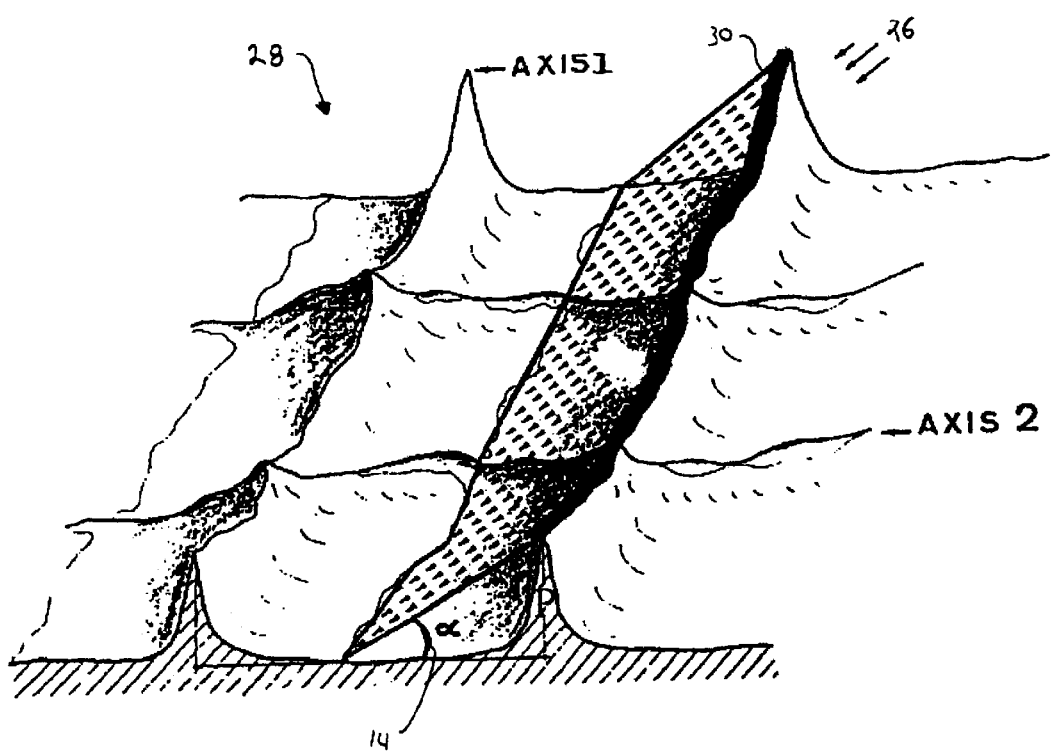
FIG. 2 is a hypothetical close up representation of a section of a skin surface replica (skin impression side of a silicone rubber mold)) made for use in a method of the present invention.

The baseline silicon replica is compared to the subsequent series of replica obtained from the patient. As shown by FIG. 1, a silicon replica 10 is placed on a horizontal surface 22 on a table 24 under a digital imaging camera 16, held up by support 18. The replica 10 is illuminated by light from a light source 12 orientated at an angle 14 (35° is a preferred angle) from the horizontal (and perpendicular to the major skin lines) thereby generating shadows due to the negative impressions of lines, wrinkles and furrows in the skin present on the replica surface, as shown by FIG. 2. In FIG. 2 the light 26 is incident upon the negative skin surface replica 28 at the angle 14. The digital camera 16 connected by means 26 to a computer 20 equipped with, for example, Quantirides software (version 2.0, Monaderm, Monaco). The Quantirides software can generate and analyze the imaged skin surface topography impression, as shown by the silicon replica. The following parameters can be calculated by the software: mean depth ($\mu$m), mean length (mm), total length (mm), number of wrinkles, surface area of wrinkles (depth×length; mm$^2$) and form factor (ratio length/depth) and used to obtain Table 1 shown below. Table 1 provides a sample of the data that can be obtained using the present method. Thus, the data that can be obtained on day 3 shows that the present method permits a determination that the onset of a muscle paralytic effect subsequent to administration of the botulinum toxin that takes place on about day 3. Additionally, as set forth by Table 1, the data that can be obtained at day 28 shows that the present method permits a determination that a peak muscle paralytic effect subsequent to administration of the botulinum toxin takes place at about day 28. Finally, as set forth by Table 1, the data that can be obtained at day 104 shows that the present method permits a determination that the duration of a muscle paralytic effect (i.e. recovery) subsequent to administration of the botulinum toxin takes place at about day 104. Thus, this example demonstrates that the facial topography method set forth in this example can be used to determine onset, peak and duration of the paralytic effect of the botulinum toxin upon a muscle, such as the frontalis muscle.

TABLE 1

|  | Baseline Measurement (pre-toxin injection/day 0) | Onset of Muscle Paralysis (measured at 3 days post-toxin injection) | Peak Muscle Paralysis (measured at 28 days post toxin injection) | Recovery (Duration of Effect) from Muscle Paralysis (measured at 104 days post toxin injection) |
|---|---|---|---|---|
| Mean Depth ($\mu$m) | 20 | 18 | 1.94 | 20 |
| Mean Length (mm) | 150 | 135 | 14.55 | 150 |
| Total Length (mm) | 175 | 157.5 | 16.97 | 175 |
| Number of wrinkles* | 8 | 7.2 | .776 | 8 |
| Surface Area of Wrinkles (mean depth × mean length; mm$^2$) | 3,000 | 2700 | 28.22 | 3,000 |
| Form Factor (ratio of mean length/mean depth) | 7.5 | 6.75 | 7.5 | 7.5 |

Example 2 sEMG Method for Determining Effect of a Botulinum Toxin Upon Frontalis Muscle

The patient in Example 1 has two pairs of surface EMG electrodes placed on the left and right frontalis and the monitor of the sEMG processor is placed within the patient's field of vision to enable the amplitude of the signal to be viewed by the patient and thereby assist with maintenance of maximum voluntary contraction.

The first electrode is placed 2 cm above the brow in a vertical line with the pupil. The second electrode is positioned laterally to the first electrode at a 45-degree angle. The inter-mid-electrode distance is 1 cm. The second electrode is placed at a 45-degree angle to be parallel with the frontalis muscle fibers to increase recording accuracy. The 45-degree angle is measured using a protractor. The recording electrodes is trimmed for ease of inter electrode spacing. The ground electrodes are placed directly in front of each ear, in the pre-auricular area. Electrode placement is shown by FIG. 3.

Surface electromyographic quantification of the frontalis muscle activation is recorded using a Neuroeducator III Surface EMG Processor. The EMG processor has independent isolated channels, each with differential amplifiers to enhance the signal to noise ratio and minimize electrical noise and 50 Hertz (Hz) artifact interference. Muscle (electrical) activity is recorded using a continuous analog integrator, read by the processor at 100 times per second, with a passband of 10–1000 Hz, assuring wideband monitoring without loss of the muscle signal. The recorded sEMG signal is full-wave rectified, and the integrated sEMG recording is displayed on the screen and stored in both graphic and numerical forms.

The same sEMG processor and disposable self-adhesive, pre-gelled Ag—AgCl surface electrodes (1 cm in diameter recording area) are used for all measurements. The active and reference electrodes are identical disposable adhesive electrodes used to record the amplitude muscle activity during maximum voluntary contraction. A new set of electrodes can be used for each patient at each visit. Additional sets are used as required to maintain good adhesion to the skin of the patient and to minimize 50 hertz Hz noise.

The method of recording enables common mode rejection by the sEMG processor, a technique that minimizes crosstalk influences on the muscle activity recorded. Prior to application of the electrodes, the skin is cleansed with alcohol to minimize 50 Hz skin impedance.

sEMG is carried out during maximum voluntary contraction of the frontalis muscle using a bipolar surface recording method and the room temperature can be maintained at approximately 20° C.

The patient is sitting in an upright relaxed position facing the sEMG monitor. This positioning can allow the patient to observe their maximum amplitude signal displayed on the monitor and assist in maintaining maximum voluntary contraction for the required duration. The patient is asked raise her eyebrows to achieve the maximum target signal and sustain it at that level for 10 seconds.

The sEMG signal obtained from the surface electrodes is processed by computer. The intensity of the responses is collected during maximum voluntary contraction of the frontalis muscle.

Surface Electromyography (sEMG) is carried out by comparing baseline sEMG studies with the results of serial sEMG studies following injection of a botulinum toxin into the frontalis muscle. The amplitude ($\mu$V) of the maximum voluntary contraction for the frontalis muscle is obtained by the sEMG recording. The Neuroeducator III surface EMG processor provides an integrated sEMG amplitude value (in $\mu$V) recorded from the electrodes placed on the right and left frontalis muscle. The sEMG recording decreases as the toxin begins its paralytic effect and increases as the effect of the toxin wears off.

The parameters that can be determined by the data from this photography analysis are onset of muscle weakness, degree of muscle weakness and recovery from muscle weakness.

Example 3

Photographic Method for Determining Effect of a Botulinum Toxin Upon Frontalis Muscle Photographs are taken of the patient in Example 1, following the sEMG procedure. At each visit, digital and 35 mm photographs frontal view of the patient's upper face are taken.

The patient is positioned in the same manner for all photographs. A stereotactic device is used to ensure consistent positioning of the face in relation to the camera which comprises a dedicated chin/head support assembly. In addition, the image obtained at the screening visit (day zero)

is used as a reference to ensure identical positioning of the head at all subsequent visits. Following positioning of the patient and verification of the set-up of the camera, the patient is requested to maximally elevate her eyebrows (by maximum voluntary contraction of the frontalis muscle) by viewing the fixed indicator. Three exposures of the full frontal view (0°) of the upper face can then be taken with both a 35 mm and with a digital camera. For all photographs lighting, framing and exposure ratios are held constant. Standardized magnification and aperture can also be used. For magnification a standardized reproduction ratio of 1:5 (35 mm equivalent) is used for both the digital and 35 mm facial photographs. The camera aperture for all 35 mm facial photographs is at f/16, and for all digital facial photographs the camera aperture is set at f/32.

The 35 mm photographic images are digitally scanned and analyzed in the same way as the digital photographs. All photographic images are calibrated and analyzed using both Mirror DPS (Canfield Scientific, Inc., Fairfield, N.J.) and Image Pro Plus (Media Cybernetics, Silver Spring, Md.). The software can draw a horizontal line through the inner canthus of the eyes and calculate the distance in millimeters between this line and the lower edge of the eyebrow at three specific points. Images from a patient are re-sized and adjusted to the same magnification as the baseline image using Mirror DPS, i.e. all images for a patient is identically sized. Images are then exported to Image Pro Plus and rotated such that a straight blue line intersects the inner canthus of the eyes.

A reduction in brow mobility (in mm) during maximal voluntary contraction is used to show onset, peak and duration of the paralytic effect. Photography is carried out by comparing baseline 2 dimensional digital (2D) and 35 mm image studies with results of serial 2D and 35 mm image studies following injection of the botulinum toxin into the frontalis muscle.

Response is determined by comparing baseline 2 dimensional digital (2D) and 35 mm image studies with results of serial 2D and 35 mm photographical image studies following injection of a Clostridial toxin into the frontalis muscle.

The reduction of the upward mobility of the eyebrow measured during maximum eyebrow elevation is obtained using the following measurement. The parameters determined by the data from this photography analysis are onset of muscle weakness, degree of muscle weakness and recovery from muscle weakness.

Although the present invention has been described in detail with regard to certain preferred methods, other embodiments, versions, and modifications within the scope of the present invention are possible. For example, a wide variety of skin muscles can be injected and their overlying or adjacent skin surface areas examined by the disclosed method.

Accordingly, the spirit and scope of the following claims should not be limited to the descriptions of the embodiments of my invention set forth above.

I claim:

1. A method for determining a pharmocodynamic effect of a botulinum toxin upon a facial muscle, the method comprising the steps of:
   (a) making an first surface electromyographic recording of electrical activity of the facial muscle into which a botulinum toxin will be injected, the recording being carried out while the facial muscle is at a first maximum voluntary contraction;
   (b) making a first impression of a skin surface in proximity to the facial muscle into which the botulinum toxin will be injected, the first impression being made while the muscle is at the first maximum voluntary contraction;
   (c) carrying out a first photographing step of the skin surface in proximity to the facial muscle into which the botulinum toxin will be injected, the first photographing step being carried out while the facial muscle is at the first maximum voluntary contraction;
   (d) injecting a botulinum toxin into the facial muscle;
   (e) making a second surface electromyographic recording of electrical activity of the facial muscle into which the botulinum toxin was injected, the second recording being carried out while the facial muscle is at a second maximum voluntary contraction;
   (f) making a second impression of the skin surface in proximity to the facial muscle into which the botulinum toxin was injected, the second impression being made while the muscle is at the second maximum voluntary contraction;
   (g) carrying out a second photographing step of a skin surface in proximity to the facial muscle to which the botulinum toxin was administered, the second photographing step being carried out while the facial muscle is at the second maximum voluntary contraction;
   (h) examining the recordings, impressions and photographs, wherein examining the impressions comprises a step of illuminating the impressions with a single light source and obtaining from the impressions mean depth, mean length, total length, number of wrinkles, surface area and form factor skin surface characteristics, and;
   (i) determining onset of paralysis, peak paralysis and duration of paralysis of the facial muscle by the botulinum toxin.

2. The method of claim 1, wherein the making an impression step comprises a step of applying a polymeric material to the skin surface to thereby obtain a mold which has, on the surface of the mold in contact with the skin surface, a negative replica of a skin surface topography.

3. The method of claim 1, where the determining step further comprises determining an extent of a diffusion of the Clostridial toxin in a muscle to which the botulinum toxin is administered and into a surrounding area.

4. The method of claim 1, wherein the botulinum toxin is a botulinum toxin type A.

5. A method for determining a paralytic effect of a botulinum toxin upon a facial muscle, the method comprising the steps of:
   (a) making a first surface electromyographic recording of an electrical activity of a facial muscle into which a botulinum toxin will be injected, the recording being made while the muscle is at a first maximum voluntary contraction;
   (b) making a first impression of a skin surface in proximity to the facial muscle into which the botulinum toxin will be injected, the impression being made while the muscle is at the first maximum voluntary contraction;
   (c) administering the botulinum toxin to the facial muscle by intramuscular injection;
   (d) making a second electromyographic recording of an electrical activity of the facial muscle into which the botulinum toxin was injected, the recording being made while the facial muscle is at a second maximum voluntary contraction;

(e) making a second impression of the skin surface in proximity to the facial muscle to which the botulinum toxin was injected, the impression being made while the facial muscle is at the second maximum voluntary contraction;

(d) examining the recordings and the impressions, wherein examining the impressions comprises a step of illuminating the impressions with a single light source and obtaining from the impressions mean depth, mean length, total length, number of wrinkles, surface area and form factor skin surface characteristics, and;

(e) determining onset of paralysis, peak paralysis and duration of paralysis of the facial muscle by the botulinum toxin.

6. The method of claim 5, further comprising a step of photographing the skin surface.

7. The method of claim 5, wherein the botulinum toxin is a botulinum toxin type A.

8. A method for determining a paralytic effect of a botulinum toxin upon a facial muscle, the method comprising the steps of:

(a) making a first impression of a skin surface in proximity to the facial muscle into or in the vicinity of which a botulinum toxin will be administered, the impression being made while the muscle is at the first maximum voluntary contraction;

(b) administering the botulinum toxin to the facial muscle;

(c) making a second impression of the skin surface in proximity to the facial muscle, the impression being made while the facial muscle is at the second maximum voluntary contraction;

(d) examining the impressions, wherein examining the impressions comprises a step of illuminating the impressions with a single light source and obtaining from the impressions mean depth, mean length, total length, surface area and form factor skin surface characteristics, and;

(e) determining onset of paralysis, peak paralysis and duration of paralysis of the facial muscle by the botulinum toxin.

* * * * *